US012776418B2

(12) United States Patent
Tschulena et al.

(10) Patent No.: US 12,776,418 B2
(45) Date of Patent: Oct. 27, 2026

(54) MEDICAL DEVICE AND COMPUTER-IMPLEMENTED METHOD OF PREDICTING RISK, OCCURRENCE OR PROGRESSION OF ADVERSE HEALTH CONDITIONS IN TEST SUBJECTS IN SUBPOPULATIONS ARBITRARILY SELECTED FROM A TOTAL POPULATION

(71) Applicant: Fresenius Medical Care Deutschland GmbH, Bad Homburg (DE)

(72) Inventors: Ulrich Tschulena, Frankfurt am Main (DE); Francesco Bellocchio, Casaletto (IT); Luca Neri, Milan (IT); Wencke Armsen, Eppstein (DE); Carlo Barbieri, Crema (IT)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 562 days.

(21) Appl. No.: 16/754,579

(22) PCT Filed: Oct. 5, 2018

(86) PCT No.: PCT/EP2018/077069
§ 371 (c)(1),
(2) Date: Apr. 8, 2020

(87) PCT Pub. No.: WO2019/072692
PCT Pub. Date: Apr. 18, 2019

(65) Prior Publication Data

US 2020/0258639 A1 Aug. 13, 2020

(30) Foreign Application Priority Data

Oct. 12, 2017 (EP) .................................... 17196137

(51) Int. Cl.
*G16H 50/70* (2018.01)
*G16H 10/60* (2018.01)
(Continued)

(52) U.S. Cl.
CPC ............. *G16H 50/70* (2018.01); *G16H 10/60* (2018.01); *G16H 20/30* (2018.01); *G16H 20/40* (2018.01);
(Continued)

(58) Field of Classification Search
CPC ........ G16H 50/70; G16H 10/60; G16H 20/30; G16H 20/40; G16H 20/60; G16H 50/30; G16H 50/50; G16H 50/80
See application file for complete search history.

(56) References Cited

U.S. PATENT DOCUMENTS 6,059,724 A * 5/2000 Campell ................ G16H 50/50 128/923
9,839,360 B2 * 12/2017 Rebec ................ A61B 5/14532
(Continued)

FOREIGN PATENT DOCUMENTS

CN 102246197 11/2011
CN 107239665 A 10/2017
(Continued)

OTHER PUBLICATIONS

Indian Office Action.
(Continued)

*Primary Examiner* — Eliza A Lam
(74) *Attorney, Agent, or Firm* — Kilyk & Bowersox, P.L.L.C.

(57) ABSTRACT

A computer-implemented method of generating a generalized model for adaptively predicting occurrence or progression of a first adverse health condition for a first subpopulation arbitrarily selected from a total population, includes
(Continued)

extracting information about characterizing features of a plurality of second subpopulations, about occurrences and/or severity of the first adverse health condition found therein and/or about corresponding prognostic results, from a plurality of publications. One or more of the characterizing features are associated with corresponding first factors indicating a relation with an adverse or beneficial contribution of the characterizing feature to the occurrence or progression of the first adverse health condition, and with corresponding second factors indicating the relative frequency of occurrence in the respective second subpopulation considered in the respective publication. The characterizing features and their first and second factors are combined into a generalized model for the total population, including calculating a baseline risk of patient. The generalized model is stored on a computer accessible and readable medium in a retrievable manner.

30 Claims, 6 Drawing Sheets

(51) Int. Cl.

| | |
|---|---|
| ***G16H 20/30*** | (2018.01) |
| ***G16H 20/40*** | (2018.01) |
| ***G16H 20/60*** | (2018.01) |
| ***G16H 50/30*** | (2018.01) |
| ***G16H 50/50*** | (2018.01) |

(52) U.S. Cl.
CPC ............ *G16H 20/60* (2018.01); *G16H 50/30* (2018.01); *G16H 50/50* (2018.01)

(56) References Cited

U.S. PATENT DOCUMENTS

| | | | | |
|---|---|---|---|---|
| 2006/0173663 | A1* | 8/2006 | Langheier .............. | G16H 50/50 703/11 |
| 2008/0114564 | A1* | 5/2008 | Ihara ...................... | G06F 16/35 702/158 |
| 2009/0144089 | A1* | 6/2009 | Heywood .............. | G16H 10/20 705/2 |
| 2014/0095201 | A1 | 4/2014 | Farooq et al. | |

FOREIGN PATENT DOCUMENTS

| | | |
|---|---|---|
| EP | 0563654 | 10/1993 |
| JP | 2017117469 | 6/2017 |
| WO | WO 2014/047570 A1 | 3/2014 |

OTHER PUBLICATIONS

European Office Action.

Doi, S.A.R., et al.; Modeling Binary Outcomes, Logistic Regression; Methods of Clinical Epidemiology; May 14, 2014; pp. 141-161; Chapter 10.

Choy, M., et al.; Estimating Disease Prevalence Using Census Data; Epidemiology and Infection; Sep. 17, 2007; pp. 1253-1260; vol. 136; No. 9; United Kingdom.

Davila-Payan, Carlo, et al.; Estimating Prevalence of Overweight or Obese Children and Adolescents in Small Geographic Areas Using Publicly Available Data; Preventing Chronic Disease; Jan. 1, 2015; vol. 12.

* cited by examiner

MEDICAL DEVICE AND COMPUTER-IMPLEMENTED METHOD OF PREDICTING RISK, OCCURRENCE OR PROGRESSION OF ADVERSE HEALTH CONDITIONS IN TEST SUBJECTS IN SUBPOPULATIONS ARBITRARILY SELECTED FROM A TOTAL POPULATION

TECHNICAL FIELD

The present method and apparatus relates to predicting occurrence or progression of adverse health conditions in test subjects, and for supporting therapy control and adjustment of such adverse health condition.

BACKGROUND

Medical-related information may originate from a plurality of different sources, such as clinical data or non-clinical data. Medical-related information may be used by health care professionals for the prescription and analysis of tests and/or for the diagnosis and treatment of diseases or medical events or, more generally, adverse health conditions. Medical-related information may also be used for assessing the risk of acquiring diseases, of existing diseases to aggravate, or of suffering from an adverse medical event. Health Risk Forecasting is a procedure aiming to analyze the probability of occurrence of a certain type of medical risk based on certain types of medical-related information. For example, Health Risk Forecasting can be used to analyze the probability of acquiring a lung disease based on whether or not a person is a smoker.

A number of studies and clinical tests have been published in which the progression of adverse health conditions and their ultimate outcome has been recorded along with various medical and other parameters characterizing the studied subjects. Some of the studies tried to find numerical algorithms for predicting the occurrence and progression of adverse health conditions and their ultimate outcome by aligning the medical and other parameters of a test subject with those that have been recorded earlier.

Some algorithms suffer from being based on data obtained from peer groups that are not representatively selected across the entire population. Thus, their predictive potential for test subjects whose medical and other parameters do not correspond to those of the peer group is limited. Additionally, certain current algorithms cannot promptly or easily be directly updated with emerging scientific evidence concerning certain medical-related information.

SUMMARY

It is, therefore, desirable to provide a computer-implemented method of generating a generalized model for adaptively predicting occurrence or progression of a first adverse health condition for a first subpopulation arbitrarily selected from a total population. Further, it is desirable to provide a computer-implemented method of adaptively predicting occurrence or progression of a first adverse health condition for a first subpopulation arbitrarily selected from a total population. Yet further it is desirable to provide a medical device implementing the computer-implemented method of generating a generalized model and a medical device implementing the computer-implemented method of adaptively predicting occurrence or progression of a first adverse health condition for a first subpopulation arbitrarily selected from a total population. Yet further it is desirable to provide a therapy control support system for supporting decision-making in respect of therapeutic measures in response to a predicted occurrence or progression of the first adverse health condition, as well as for supporting patient-specific adaptation, or personalization, of such therapeutic measures.

The expression first adverse health condition is used herein to describe one or more from the non-exhaustive list comprising cardiovascular event (CVE), chronic kidney disease (CKD), all cause hospitalizations, fractures, injuries, falls, infections, need for renal replacement therapy (e.g. dialysis or transplantation), end-stage renal disease, acute kidney injury, graft failure, vascular access complications, other disease outcome, etc.

In parts of the following description reference is exemplarily made to predicting of occurrence of chronic kidney disease (CKD) in a subpopulation and/or prediction of progression of CKD across various stages of severity, eventually into end stage renal disease (ESRD) and kidney failure. However, the same principles, methods and systems discussed herein below can be used for other adverse health conditions as exemplarily listed above. For example, the same method can be applied to prediction of cardiovascular events/hospitalization occurrence among patients with chronic kidney disease.

The expression first subpopulation as used herein refers to an individual having traits, attributes, or other characterizing features which allow distinguishing the individual from other members of a total population. Instead of referring to an individual it may also refer to a group of individuals sharing the same traits, attributes, or other characterizing features, distinguishing the group from other members of the total population. The total population comprises a plurality of second subpopulations, e.g., subpopulations considered in respective scientific studies, in literature or the like. The total population may comprise all second subpopulations for which data is available for analysis. Different second subpopulations may or may not share one or more traits, attributes or other characterizing features with the first subpopulation or other second subpopulations. However, each subpopulation will differ in at least one trait from any other subpopulation. Second subpopulations separately analyzed in individual studies or pieces of literature in respect to the same adverse health conditions may be partially overlapping or may even be identical.

As stated above the expression characterizing features as used herein refers to traits, attributes, which allow distinguishing an individual or group of individuals from other individuals or groups of individuals. Characterizing features may include general information characterizing individuals or a population, genetic information, e.g. obtained from genetic marker analysis systems, medical events and states, treatments, diagnosis, and prognosis characterizations, etc. The characterizing features may thus include demographic data, e.g., age, race, sex, work place, environmental factors, place and circumstances of residence, life style, etc. Likewise, self-reported data, e.g., from surveys captured intermittently from individuals or members of a population, which surveys may relate to perceived quality of health status, prescription drug information, e.g., types and/or amount of prescription drugs taken by an individual or a population, data obtained from diagnostic records, e.g., previous hospitalizations, clinical tests and results, and treatment data, e.g., illness, type, times and place of treatment, hospital, and/or doctor, etc., can be used as characteristic features for distinguishing an individual or a group of subjects from other individuals or groups of subjects. In addition, medical data may be used as characterizing feature, e.g. glomerular filtration rate, albuminuria, blood pressure, comorbidities, e.g., diabetes, hypertension or congestive heart failure, as well as etiology of diseases, e.g., glomerulonephritis. Other medical data useful as characterizing feature includes change of glomerular filtration rate over time, phosphate levels, bicarbonate, albumin, cholesterol, C-reactive protein, serum creatinine or calcium levels. Such medical data may be obtained from any kind of routine or advanced diagnostic test including but not limited to any imaging technique (e.g. magnetic resonance imaging, sonography, x-ray, CT scan, scintigraphy, etc), electrophysiology testing, physical examination results, immunoassays and radioimmunoassay systems, biochemistry, polymerase (PCR) chain reaction analysis systems, chromatography analysis systems, and/or receptor assay systems, etc. Data from other analysis systems, such as tissue analysis systems, cytology and tissue typing systems, and immunocytochemistry and histopathological analysis systems may also be included. The characterizing features may be time-invariant or relate to current and/or past time instants. The characterizing features may also relate to a grade or level of severity of an adverse health condition. The data may also be provided as a time series or as a derivative thereof, indicating a change over time. Generally, any kind of information that is suitable for classifying patients can be used as characterizing feature.

In accordance with an aspect the computer-implemented method of generating a generalized model for adaptively predicting occurrence or progression of a first adverse health condition arbitrarily selected from a total population described herein includes executing computer program instructions in a computer comprising one or more microprocessors, volatile and/or non-volatile memory and one or more data and/or user interfaces, for extracting information about characterizing features of a plurality of second subpopulations, about occurrences and/or severity of the first adverse health condition found therein and/or about corresponding prognostic results, from a plurality of publications and/or primary clinical data recorded in electronic databases and elaborated according to probabilistic statistical models. One or more characterizing features, e.g. those known to be useful in the respective context, may be provided as further input for initializing the extraction, but this is not a strict requirement, since the extraction itself may identify other or further characterizing features as also or equally relevant, or even more relevant. The computer program instructions may configure the computer executing those instructions to provide an extraction module. The extraction module may control or cooperate with various interfaces for accessing publications and/or clinical data records and the like. The interfaces include one or more of data communication interfaces, cameras, scanners and the like.

The term publication is used herein to describe scientific studies and papers, general literature or literature with a focus on health issues, data sets correlating health issues with patient's properties that can be unambiguously linked with one or more patients: Such properties include but are not limited to age, gender, height, weight, BMI, use of substances or alcohol, smoking, history of hypertension or hypotension, diabetes, COPD, lung cancer, CKD stage, history of cerebrovascular disease, coronary artery disease, peripheral artery disease, chronic heart failure, chronic obstructive pulmonary disease, autoimmune disorders, anxiety/depression, cancer, liver disease, BMI, albumin, glucose, HDL, LDL, Triglycerides, CRP, IL-6, serum uric acid, HsTNT, Phosphate, iPTH, proteinuria and albuminuria, other known chronic diseases, past cured diseases, behavior or lifestyle, psychological profiles, morphological characteristics assessed via any imaging technique, or functional characteristics assessed via any appropriate diagnostic testing. The list provided hereinbefore is non-exhaustive and may represent a subset of characterizing features cited further above.

The information about characterizing features extracted from the plurality of publications and/or primary clinical data recorded in electronic databases and elaborated according to probabilistic statistical models may comprise those patient's properties which show a positive or negative correlation with regard to the first adverse health condition.

The method further includes executing computer program instructions in a computer for associating, based on data from each of the plurality of publications and/or primary clinical data recorded in electronic databases and elaborated according to probabilistic statistical models, one or more of the characterizing features identified therein with corresponding first factors indicating a relation with an adverse or beneficial contribution of the characterizing feature to the occurrence or progression of the first adverse health condition. The first factors may accordingly be represented, e.g., by effect size measures such as odds ratios, hazard ratios, relative risks.

The relation indicated by the first factor may express a risk increase or decrease for occurrence or progression of the first adverse health condition in a patient, e.g. expressed with respect to a reference population, either healthy or in an appropriately selected peer group, expressed as a value generated by comparing to a baseline model in which that particular characteristic feature is absent or at a "normal" level, or as an absolute risk.

The method further includes associating, from each of the plurality of publications and/or primary clinical data recorded in electronic databases and elaborated according to probabilistic statistical models, one or more of the characterizing features identified therein with corresponding second factors indicating the relative frequency of occurrence, or prevalence, in the respective second subpopulation considered in the respective publication. The combination of data on characterizing features and associated first and second factors over a plurality of publications and/or primary clinical data recorded in electronic databases and elaborated according to probabilistic statistical models may provide an indication for a likelihood of occurrence or progression in the total population. The computer program instructions may configure the computer executing those instructions to provide an associator module adapted to execute the association steps. The associator module may implement various probabilistic statistical models that are selectable in accordance with the first adverse health condition, the type of data and/or characterizing features and the like.

The method further includes executing computer program instructions in a computer for combining the characterizing features and their first and second factors into a generalized model for the total population, wherein combining includes calculating a baseline risk of a virtual "general" member of the total population and estimating the conditional probability of a first adverse health condition for all the potential configurations of known health states contributing to the first adverse health event risk. A baseline risk may be considered a general risk for the virtual "general" member of the total population in which all identified and known risk factors are absent or at their lowest possible values. The computer program instructions may configure the computer executing those instructions to provide a combiner module adapted to execute the combining steps. The combiner module may implement various probabilistic statistical models that are selectable in accordance with the first adverse health condition, the type of data and/or characterizing features and the like.

The combination of the characterizing features and their first and second factors may follow the steps exemplarily described hereafter.

In the case of effect sizes expressed as odds ratios, input to the process is adverse outcome incidence I risk factor prevalence $P_1, P_2, \ldots, P_n$ effect size measures: $OR_1, OR_2, \ldots, OR_n$ Output of the process is conditional probabilities of risk factors $P_{RF\_1}, P_{RF\_2}, \ldots, P_{RF\_n}$ for a given outcome The procedure may be briefly summarized as 1. Get I
2. Get $P_1, P_2, \ldots, P_n$
3. Get $OR_1, OR_2, \ldots, OR_n$
4. Compute for each risk factor the contribution to the outcome risk as $$W\_RF_i = \ln(OR_i) \times P_i$$

5. Compute base risk as $\lambda = -\ln((1-I)/I) - \Sigma_i W\_RF_i$
6. Compute the probability of the outcome given each risk factor as $$P\_O_{RF\_i} = \exp(\Sigma_{j \neq i} W\_RF_j + \ln(OR_i) + \lambda)/(1 + \exp(\Sigma_{j \neq i} W\_RF_j + \ln(OR_i) + \lambda))$$

7. Compute the joint probability of outcome and each risk factor as $$P\_O\_RF_i = P\_O_{RF\_i} \times P_i \text{(Bayes' theorem)}$$

8. Compute the probability of each risk factor given the outcome as $$P_{RF\_i} = P\_O\_RF_i / I$$

It is to be noted that the same methodology can be extended to a variety of statistical models that are derived from exponential distribution families. Likewise, other statistical computations may be used to combine the various characterizing features and their respective first and/or second factors into a generalized model or for computing a baseline risk, depending on the set of characterizing features considered.

The method further includes storing the generalized model in a retrievable manner on a computer accessible and readable medium. To this end the method may include executing computer program instructions in a computer for providing a communication module. The communication module may control or cooperate with various interfaces for accordingly accessing data storage media.

In other words, the aspect of the method presented above selects the most relevant information from a vast array of available publications and/or primary clinical data recorded in electronic databases and elaborated according to probabilistic statistical models, like clinical and patient-reported data, assesses the contribution of patient-specific health-state attributes to future risk, creates a generalized model, including a baseline reference, and stores the model for future application using a subpopulation's attributes as input values. Generalized models for different adverse health conditions may differ in the characterizing features represented therein, mostly depending on their respective impact on the likelihood of occurrence or progression of that particular adverse health condition. The generalized model may include the baseline risk and data indicating the contribution of each or a selected number of characteristic features to a risk increase or decrease.

In an aspect of the method weights are derived and associated with the first and/or second factors. The weights may be derived from data from a single publication or with respect to a plurality of publications, or a mixture of a plurality of publications and primary clinical data recorded in multiple electronic databases and elaborated according to probabilistic statistical models.

In an aspect of the method extracting includes automatic extraction using one or more of electronic text processing, optical character recognition, natural language processing, but also manual data entry. In case of automatic extraction of characterizing features rule-based extraction or extraction assisted by artificial intelligence as well as other methods may be used. The computer program instructions may configure the extraction module to provide one or more of the above-mentioned functionalities or provide access thereto.

In an aspect of the method the characterizing features and the associated factors are adjusted, ranked and/or selected for the quality of the publication prior to generating the generalized model. The quality of the publication and the primary dataset source may be assessed by considering the number of participants analyzed, the risk of bias through standardized procedures, the absence of conflict of interests by the authors, and the like.

In an aspect of the method the characterizing features and the associated factors are adjusted, ranked and/or selected for the conditional probability of an outcome associated with a single characterizing feature across the plurality of publications. In other words, a summary view of the significance of same characterizing feature across the plurality of publications and/or a mixture of publications and probabilistic analyses of primary clinical data is provided.

In an aspect of the method the characterizing features and the associated factors are adjusted, ranked and/or selected differently for different prognosis time periods, thereby adapting to findings that individual characterizing features may have different value or reliability for different prognosis time periods. This may reduce the number of characterizing features or parameters that need to be monitored and fed to the prediction and thus reduces the computational efforts. When no prognosis time period or prediction time period is provided one or more preset prediction or prognosis time periods may be used and according models may be generated.

For example, a list of most influential characterizing features or parameters for a prediction time period of 2 years for progression of chronic kidney disease into end stage renal disease includes glomerular filtration rate gradient, glomerular filtration rate (GFR), proteinuria, weight, hemoglobin, Charlson index, and serum phosphate, with the first three being very influential for the prediction. A list of most influential characterizing features or parameters for a prediction time period of 5 years for progression of chronic kidney disease into end stage renal disease includes systolic pressure, diastolic pressure, serum phosphate, GFR, serum calcium, proteinuria, PTH, serum albumin, heart rate, with the first four being very influential for the prediction. It is easy to see that different prediction time periods require different sets of characterizing features or parameters, or at least giving different weights to the characterizing features or parameters. This information on its own may be useful in providing support to a physician in determining or deciding which characterizing features to monitor more closely or to apply additional tests for, when using the general model for predicting occurrence or progression of the adverse health condition. By calculating predicted probability variation associated with each characterizing feature for each individual patient, the method also allows creating a patient-specific ranking of the prognostic value of each characterizing feature contributing to outcome prediction for each individual patient. In this way the physician is supported in planning a personalized diagnostic evaluation strategy for each individual patient that maximized prognostic accuracy while reducing the number of diagnostic testing needed to describe patient's health state.

Similarly, in an aspect of the method the characterizing features and the associated factors are adjusted, ranked and/or selected differently for a specific first adverse health condition and/or a severity or current stage of the first adverse health condition. For example, when a first adverse health condition can assume different levels of severity or different stages, characterizing features may have different value or reliability for predicting the risk of progression of the adverse health condition into the next level of severity or stage.

Thus, the method may include executing computer program instructions in a computer for providing a priming module that is adapted to receive input corresponding to selecting a prediction time period and/or a current level of severity or stage of the adverse health condition. The input from the priming module may be used for selecting one of a variety of statistical models for generating the generalized model in accordance with the priming input. For example, when an adverse health condition is generally divided into five different stages of severity the priming input may be used for generating a generalized model for progression of the adverse health condition from level 3 to level 4. This input may result in selecting the second subpopulation for data input accordingly, excluding those subpopulations from consideration that are not suitable, e.g., because the adverse health condition does not progress skipping levels.

The plurality of publications subjected to the method described above may be limited to those publications in which the adverse health condition has been mentioned, or considered, irrespective of whether a positive, negative or no correlation between the first adverse health condition and the patient's properties analyzed in the publication has been found. This may serve as a pre-selection for enhancing the quality of the prediction, or for accelerating the execution of the method. Thus, in an aspect of the method, as a further step, the result of a first run of the method, e.g. a characterizing features correlated with an adverse health condition, including those found across the plurality of the publications that was not apparent from any single publication taken alone, may be taken as an input for re-running the method including those publications that had previously not been considered, e.g. in order to find an unlikely and previously unknown correlation between an adverse health condition and a further characterizing feature.

Similarly, in an aspect of the method described above a periodic or event-triggered check for new publications is executed, e.g. by scanning publications for the occurrence of a term or expression or synonym for the adverse health condition or one or more of the characterizing features previously identified, which are related to the adverse health condition. Whenever such new publication is found data is extracted in the way described further above, and the data is input to the method for re-running the steps for generating the generalized model.

The method allows for easy iterative adjustment and improvement by adding new aggregate data to the initial evidence base extracted from clinical studies, real world evidence, or pieces of literature. Such continuous fine-tuning of the existing model is feasible because the model generation process can be solely based on population summary measures. The prominent advantage of this literature-based analysis approach compared traditional data-driven approaches is that it is optimized to fully rely on published, publicly available aggregated data for model derivation or update and does not need enumerating and following up a new cohort for model derivation or update, an expensive, time-consuming and often unfeasible endeavor. Even though not strictly necessary, analysis of primary clinical data may optionally be used to complement the model obtained through literature review. The model parameters can be easily re-calculated using the same methods as described in the sections above, by simply adding the new aggregate data measure extracted from any eligible new study to the full evidence base previously used to derive the model.

Several aspects of the method described hereinbefore may be combined with each other and/or may be integrated in the underlying method. E.g., the two-run aspect may be combined with adjusting, ranking and/or selecting characterizing features.

Once the generalized model has been generated it may be used in a computer-implemented method of adaptively predicting occurrence or progression of a first adverse health condition for an arbitrarily selectable first subpopulation of a total population. In an aspect this method includes executing computer program instructions in a computer for receiving one or more characterizing features from a generalized model generated and stored in a computer accessible and readable memory in accordance with the method of generating a generalized model for adaptively predicting occurrence or progression of a first adverse health condition arbitrarily selected from a total population described further above. The computer executing the computer program instructions may represent a therapy control support system. The characterizing features may be those identified as risk factors, which have at least some correlation with the adverse health condition currently under consideration, either beneficial or aggravating. The selection of characterizing features to be received may reflect a current grade or level of severity present in the first subpopulation, e.g., for predicting progression of the adverse health condition to a next stage, or may reflect a prediction time period. The selection of characterizing features for progression of the adverse health condition into the next stage or for the prediction time period may effectively be a selection of a limited set of or even a single characterizing feature that had been found being useful predictors. The selected characterizing features may be different for predicting progression of the adverse health condition into different next stages or for different prediction time periods. The computer program instructions may configure the computer executing those instructions to provide and/or control a communication module. The communication module may control or cooperate with various hardware and/or software interfaces for receiving the one or more characterizing features and/or the generalized model from a data base.

The method of adaptively predicting occurrence or progression of a first adverse health condition for an arbitrarily selectable first subpopulation of a total population further includes executing computer program instructions in a computer for receiving data characterizing the first subpopulation. The data characterizing the first subpopulation may comprise all or a subset of the characterizing features required, provided, used, analyzed or considered in the generation of the generalized model. The data characterizing the first subpopulation may thus include data representing physiological features, demographic information, comorbidities, complications and medications, e.g. age, sex, intake of alcohol, smoking, BMI, history of hypertension, diabetes, CKD stage, history of cerebrovascular disease, coronary artery disease, peripheral artery disease, chronic heart failure, chronic obstructive pulmonary disease, autoimmune disorders, anxiety/depression, cancer, liver disease, levels of Albumin, Glucose, HDL, LDL, Triglycerides, CRP, IL-6, S-Uric Acid, HsTNT, Phosphate, iPTH, proteinuria and Albuminuria. It is to be noted that the first subpopulation for this method need not be the same first subpopulation that was referred to in the method for generating the generalized model, and that not all characterizing data need to be used or may even be available. The data characterizing the first subpopulation may be received through the communication module, and the computer program instructions may control the communication module accordingly.

The method further includes providing the one or more received characterizing features from the generalized model and the data characterizing the subpopulation to a computing module implementing a probabilistic model or, more generally, to a predictor module. The computing or predictor module may be implemented as a computer executing corresponding software, either exclusively or in a dedicated thread that runs in parallel to other tasks on the computer. The probabilistic model may be one of a plurality of known models, e.g. a Bayesian network. The probabilistic model produces, or calculates, as an output signal, a summary score indicating a risk, or a probability, of occurrence or progression of the adverse health condition for the first subpopulation. The risk, or probability, may be provided as an absolute value, or as a relative value, e.g. over a population in which all risk factors are absent. Characterizing features present in the generalized model but not available for the first subpopulation under consideration may be ignored or assumed in accordance with the baseline risk for those characterizing features.

The output signal is provided to a user or a computer. Providing may include displaying the result on a display screen, printing the result, acoustically providing the result, e.g. over a loudspeaker after text-to-speech conversion, and the like. Providing may also include transmitting the result over a digital communication channel to a user's computer. Providing may include controlling the communication module accordingly.

In an aspect the therapy control support system implementing the method may include providing data signals representing positive or negative effect of one or more characterizing features on the summary score, or the probability of occurrence or progression of the adverse health condition. The data signals may be provided in a ranked order in accordance with their significance of their contribution to the summary score.

In an aspect of the therapy control support system implementing the method, in case multiple characterizing features and their effect on the summary score or probability are provided, these are provided in a ranked order according to the significance of their respective contribution to the summary score for the first subpopulation under assessment, i.e. for a single patient or for a group of patients. The ranking may be by absolute or relative contribution. The contribution of a characterizing factor may be either beneficial, i.e. reducing the risk, or adverse, i.e. increasing the risk, and the ranking by significance may be by the absolute significance, irrespective of being beneficial or adverse, or grouped into beneficial and adverse characterizing factors.

In one aspect of the therapy control support system implementing the method the predictor module is further configured to adjust, weight, rank and/or select the characterizing features and the associated factors in accordance with a current stage or severity of the first adverse health condition in the first subpopulation received as a further input. This may improve the accuracy of the prediction of progression of the adverse health condition into a next, more severe stage.

In an aspect of the therapy control support system implementing the method characterizing features having positive or negative effect on the risk determined for the adverse health condition, which are modifiable through one or more responsive actions from the non-exhaustive list comprising therapy, change of lifestyle, change of diet and medical intervention, are highlighted. Highlighting may include printing in bold letters, italics, different font, different font or background color. Selective highlighting may be applied, e.g. in accordance with a ranking of how difficult a modification of a diet or a lifestyle will be for the subpopulation, or how likely an enduring adherence to the modified diet or lifestyle is. Other rankings for the highlighting may include an estimated cost for the modification, e.g. in connection with a selection of possible therapies or medical interventions.

In an aspect the therapy control support system implementing the method further includes providing information about how much the risk or the probability of occurrence or progression of the adverse health condition is modified by a responsive action, e.g. by indicating that stopping smoking or reducing weight will reduce the risk by a certain percentage. In addition, the risk reduction for different degrees of compliance with the responsive action may be indicated, e.g., reducing sugar intake by only 50% of the recommended responsive action will yield a risk reduction by 60% vs. the best possible outcome, or the like. The information may be provided through the communication module in response to data provided by the predictor module.

In an aspect the therapy control support system implementing the method is further adapted to provide a selection of therapy recommendations based on the kind of adverse health condition and/or the risk score. The selection of therapy recommendations may, for example, include closer monitoring of a patient or a subpopulation, e.g., by means of telemedicine, portable devices for monitoring bodily functions, more frequent visits to a physician or a clinic, closer supervision by a case manager, referral to a specialist, more aggressive medication therapy and the like. The selection of therapy recommendations may also be selected and/or ranked in accordance with characterizing features present in the first subpopulation and their respective contribution to the overall risk of occurrence or progression of the adverse health condition. The selection of therapy recommendations may be provided in response to a prior request to a database or artificial intelligence system connected thereto. The database stores at least one therapy recommendation for each one of a plurality of adverse health conditions.

In an aspect the therapy control support system implementing the method is further adapted to suggest a selection of additional diagnostic testing and/or therapy that could produce data related to or describing further characterizing features, results or data relating to which can be provided as an input to the method, i.e. the software module implementing the prediction, for improving the accuracy of the summary score. The selection of additional testing may be provided in a ranked order, e.g. in accordance with their level of invasiveness to a patient and/or cost, their availability in a region or location, a time until test results can be expected, and the like. Suggesting the selection of additional diagnostic testing and/or therapy may include controlling the predictor module and/or the communication module accordingly.

In an aspect the method further includes receiving a prediction time period. The prediction time period may be received at an early stage of the execution of the method and may result in selecting different sets of characterizing features and/or associated factors or weights as input for the prediction, and/or a different generalized model determined for a particular prediction time period.

Another aspect of the present disclosure includes a medical device, e.g. implemented by a computer system executing computer program instructions which implement one or more aspects of the methods describe hereinbefore. The medical device may represent a model generator of a therapy control support system and a therapy control support system, which together act as a system. Each of the medical devices may include a display and a user interface, an interface for receiving digital data, and one or more microprocessors and associated volatile and/or non-volatile memory. The interface for receiving digital data may be of conventional type and may provide connection with wired or wireless networks such as Ethernet (LAN), according to standards of the IEEE 802.11 family, also known under the trademark name 'WiFi', according to standards of the IEEE802.15 family, also known under the registered brand name 'Bluetooth', but also with portable data storage devices connected through serial or parallel connections, such as Universal Serial Bus (USB) or a connection according to IEEE 1394 (FireWire). Each of these interfaces comprises a physical transmitter and receiver part as well as a logical transmitter and receiver part, some of which may be similar in structure and operation across the various standards. The medical device may further include or being configured to access a database containing data records associating a plurality of medical risks and a plurality of health parameters and/or characterizing features, as well as other data describing the total population and/or a plurality of subpopulations. The data base may further provide access to a plurality of publications and other medical documentation.

According to one aspect of the present disclosure the medical device implementing the model generator of the therapy control support system, when the processor executes the computer program instructions, may be configured to generate a generalized model for adaptively predicting occurrence or progression of a first adverse health condition for a first subpopulation arbitrarily selected from a total population. The generalized model may represent interrelationships between a plurality of medical risks and a plurality of health parameters. In accordance with this aspect, the medical device is configured to extract information about characterizing features of a plurality of second subpopulations, about occurrences and/or severity of the first adverse health condition and/or about corresponding prognostic results found in a plurality of publications. The publications may, e.g., be obtained through accessing one or more databases. The medical device may further be configured to associate, from each of the plurality of publications, one or more of the characterizing features identified therein with corresponding first factors indicating a relation with an adverse or beneficial contribution of the characterizing feature to the occurrence or progression of the first adverse health condition, and further to associate one or more of the characterizing features with corresponding second factors indicating the relative frequency of occurrence in the respective second subpopulation considered in the respective publication. The medical device may yet further be configured to combine the characterizing features and their first and second factors into a generalized model for the total population, wherein combining includes calculating a baseline risk of a virtual "general" member of the total population, and to store the generalized model and/or the baseline risk in a retrievable manner on a computer accessible and readable medium. The baseline risk may represent a risk of occurrence or progression of the adverse health condition for a subject that does not exhibit or is not exposed to any characterizing feature that had been identified as having a negative influence on the occurrence or progression of the adverse health condition, or exhibits or is exposed to such characterizing feature to the lowest possible extent.

In an aspect of the present disclosure the medical device may be configured to perform automatic extraction of information from publications using one or more of electronic text processing, optical character recognition, and natural language processing.

In an aspect of the present disclosure the medical device may be configured to adjust, rank and/or select characterizing features and the associated factors for the quality of the publication prior to generating the generalized model. Adjusting, ranking and/or selecting may be executed in accordance with the quality of the publication, or in accordance with the conditional probability of an outcome associated with a single characterizing feature across the plurality of publications.

In an aspect of the present disclosure the medical device may be configured to, in a first run of the method, limit the plurality of publications to those considering the first adverse health condition and, in a second run of the method, to use the result of the first run as an input to the method, along with one or more publications not considering the first adverse health condition.

According to one aspect of the of the present disclosure the medical device implementing the therapy control support system, when the processor executes the computer program instructions, may be configured to adaptively predict occurrence or progression of a first adverse health condition for an arbitrarily selectable first subpopulation of a total population. In accordance with this aspect, the medical device is configured to receive one or more characterizing features from a generalized model generated and stored in a computer accessible and readable memory, e.g. in accordance with the method described further above. The medical device is further configured to receive data characterizing the first subpopulation and to provide the one or more received characterizing features from the generalized model and the data characterizing the subpopulation to a software module implementing a probabilistic model. The medical device is yet further configured to provide a summary score output from the software module, indicating a risk or probability of occurrence or progression of the adverse health condition for the first subpopulation, and to provide, to a user, one or more characterizing features and their positive or negative effect on the risk or the probability of occurrence or progression of the adverse health condition.

In an aspect of the present disclosure the medical device may be configured to provide the one or more characterizing features and their positive or negative effect on the risk or the probability of occurrence or progression of the adverse health condition in a ranked order according to their significance of their contribution to the summary score.

In an aspect of the present disclosure the medical device may be configured to highlight those characterizing features having positive or negative effect on the risk or the probability of occurrence or progression of the adverse health condition which can be modified or influenced through one or more responsive actions from the non-exhaustive list comprising therapy, change of lifestyle, change of diet and medical intervention.

In an aspect of the present disclosure the medical device may be configured to provide information about how much the risk or the probability of occurrence or progression of the adverse health condition is modified by a responsive action.

In an aspect of the present disclosure the medical device may be configured to provide a selection of therapy recommendations based on the kind of adverse health condition and/or the risk score.

In an aspect of the present disclosure the medical device may be configured to provide a selection of additional diagnostic tests and/or therapy that could produce data related to or describing further characterizing features, results or data relating to which can be provided to the software module for improving the accuracy of the summary score. The selection of additional diagnostic tests and/or therapy may be provided in a ranked order, e.g. in accordance with their cost, availability within a region or location, a time until test results are available or visible effects can be expected, and the like.

Another aspect of the present disclosure includes a computer-readable medium for use on a computer system configured to implement generating a generalized model for adaptively predicting occurrence or progression of a first adverse health condition for a first subpopulation arbitrarily selected from a total population. The computer-readable medium according to this aspect may have computer-executable instructions for performing a method including extracting information about characterizing features of a plurality of second subpopulations, about occurrences and/or severity of the first adverse health condition found therein and/or about corresponding prognostic results, from a plurality of publications, associating one or more of the characterizing features identified in each of the plurality of publications with corresponding first factors indicating a relation with an adverse or beneficial contribution of the characterizing feature to the occurrence or progression of the first adverse health condition, further associating one or more of the characterizing features with corresponding second factors indicating the relative frequency of occurrence in the respective second subpopulation considered in the respective publication, combining the characterizing features and their first and second factors into a generalized model for the total population, wherein combining includes calculating a baseline risk of patient, and storing the generalized model in a retrievable manner on a computer accessible and readable medium.

Yet another aspect of the present disclosure includes a computer-readable medium for use on a computer system configured to implement adaptively predicting occurrence or progression of a first adverse health condition for an arbitrarily selectable first subpopulation of a total population. The computer-readable medium according to this aspect may have computer-executable instructions for performing a method including receiving one or more characterizing features from a generalized model generated and stored in a computer accessible and readable memory, receiving data characterizing the first subpopulation, providing the one or more received characterizing features from the generalized model and the data characterizing the subpopulation to a software module implementing a probabilistic model, providing a summary score from the software module, indicating a risk or probability of occurrence or progression of the adverse health condition for the first subpopulation and providing, to a user, one or more characterizing features and their positive or negative effect on the risk or the probability of occurrence or progression of the adverse health condition.

Storing, receiving and/or providing as used throughout this specification may include establishing a physical and/or logical digital communication channel between a processor and a memory, between a first and a second computer over a digital communication connection or network, or combinations thereof.

The present medical devices, systems and methods may provide efficient and accurate prediction of adverse health conditions for an arbitrarily selected subpopulation or individual based on health information obtained from publications, literature and the like that focus on a limited or selected subpopulation. Such technology may be used to predict and manage individual health risks as well as to analyze and manage health risks of a group or a population.

In subjects suffering from CKD a prediction of the progression of the disease that is as accurate as possible may be useful in determining when to prepare the subject for renal supplement or replacement therapy (dialysis), since placing catheters in the abdomen or creating fistulas, grafts or other access points to the blood circuit typically requires surgery and time for healing and/or maturing.

Likewise, in patients suffering from CKD or ESRD a prediction of a risk for hospitalization may allow for a caregiver or physician to initiate measures to mitigate or even eliminate the risk of hospitalization, in particular cardiovascular hospitalization.

Patient-specific or subpopulation-specific ranking of risk factors and beneficial factors by their impact on the absolute or relative risk allows for a physician or other medical caregiver to provide more focused and more effective treatments or preventive measures.

Individual users may use the disclosed medical devices and methods to predict occurrence or progression of potential adverse health conditions based on their own health data or characterizing features. The individual users may also obtain information for reducing the risks or the likelihood of occurrence or progression of an adverse health condition changing relevant behavior, e.g., lifestyle, corresponding to its contribution to the risk or likelihood.

Group or institutional users may use the disclosed medical devices and methods to calculate health risks among a population, such as a particular distribution among the population. The institutional users may also optimize the distribution to reduce the health risks of a population and to promote healthy lifestyle.

BRIEF DESCRIPTION OF THE DRAWINGS

In the following section the method will be described with reference to the drawings. In the drawings

DESCRIPTION OF EMBODIMENTS

Reference will now be made in detail to exemplary embodiments, which are illustrated in the accompanying drawings. Wherever possible, the same reference numbers will be used throughout the drawings to refer to the same or like parts.

Figure 1:
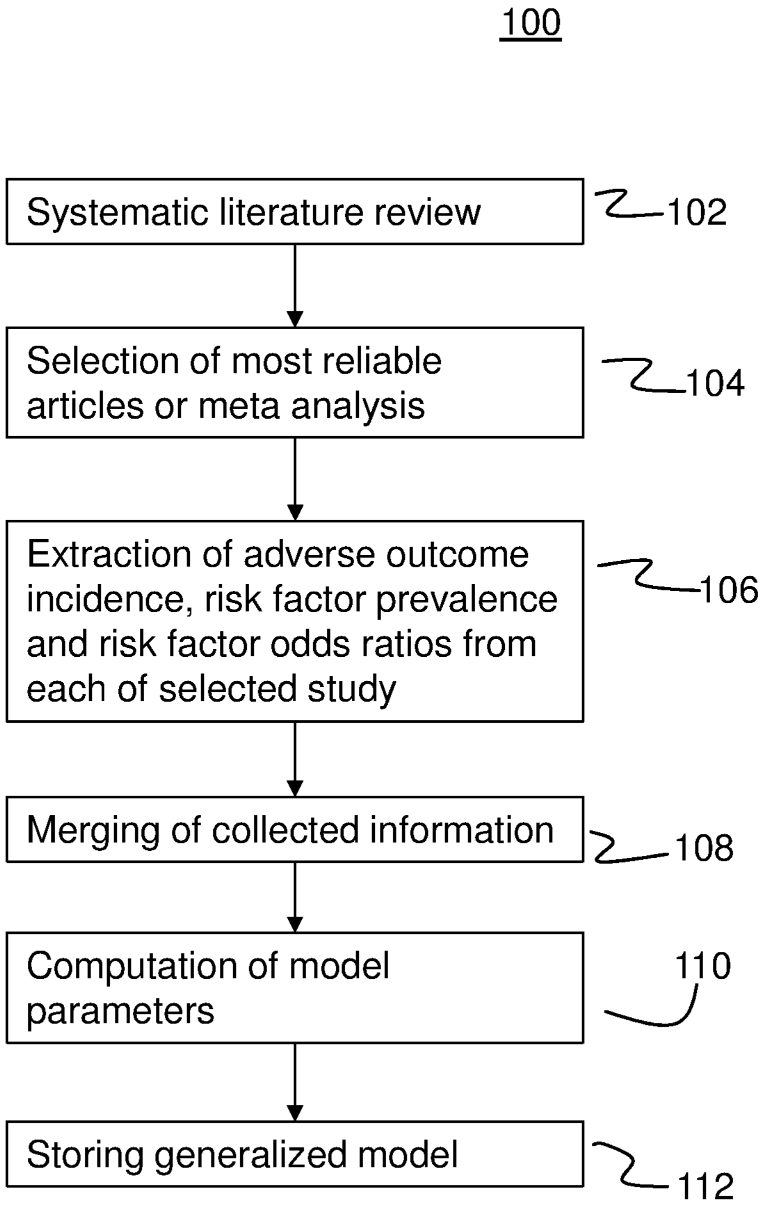
FIG. 1 illustrates a flowchart diagram of an exemplary method 100 of generating a generalized model for adaptively predicting occurrence or progression of a first adverse health condition for a first subpopulation arbitrarily selected from a total population, FIG. 2 describes a more detailed, exemplary embodiment of the selection step shown in FIG. 1.

FIG. 1 illustrates a flowchart diagram of an exemplary method of generating a generalized model for adaptively predicting occurrence or progression of a first adverse health condition for a first subpopulation arbitrarily selected from a total population. In step 102 literature or other publications, including medical records from hospitals or other health institutions, are systematically reviewed, and in step 104 the most reliable articles or meta analyses from the literature or publications are selected. From these selected documents characterizing features, e.g., adverse outcome incidence, risk factor prevalence and risk factor odds ratios, are extracted in step 106 and merged in step 108. The merged information is then used in step 110 to compute model parameters for the generalized model, which are stored in step 112. The model parameters may be computed using any appropriate type of probabilistic model, e.g., exponential family functions.

Figure 2:
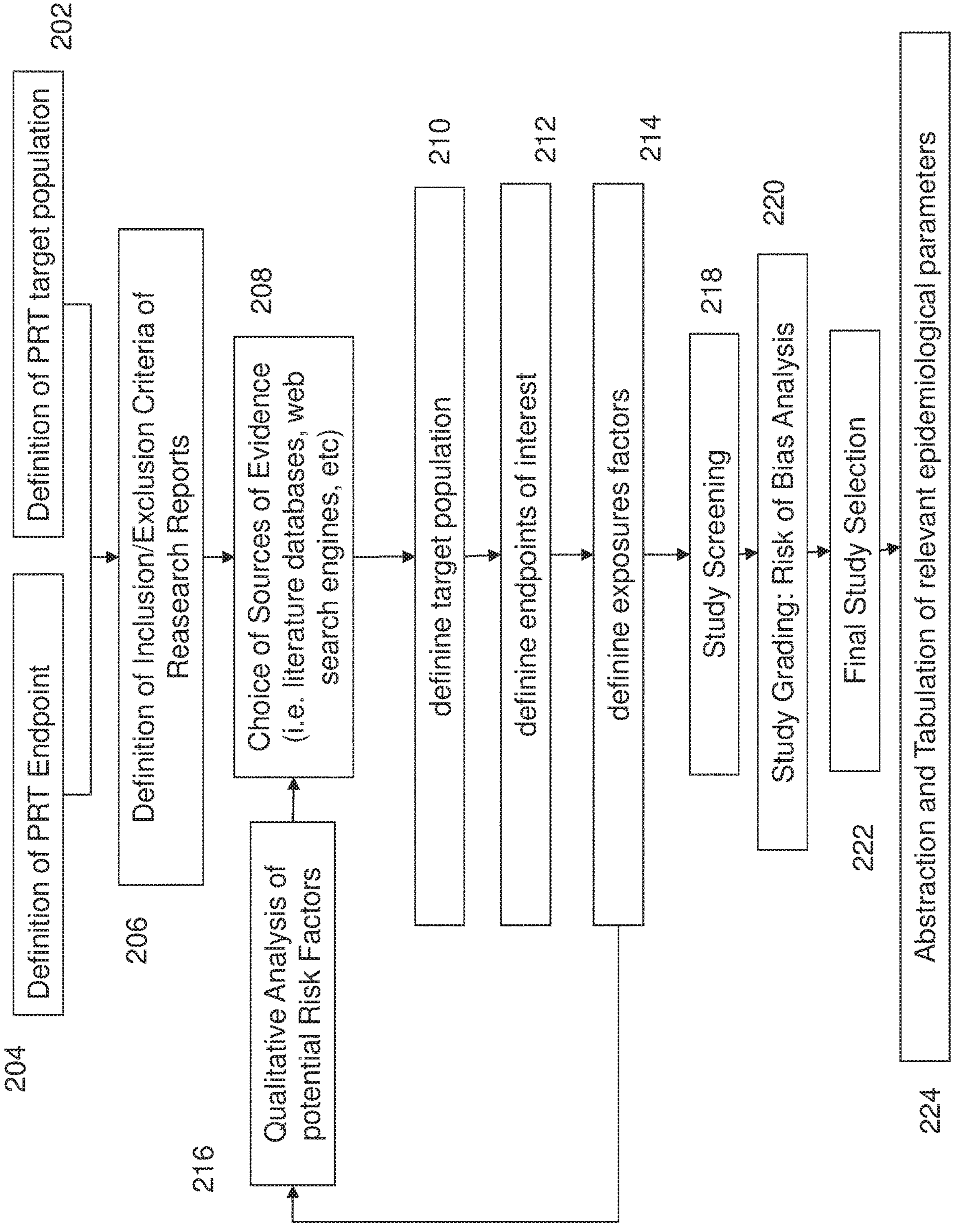

FIG. 2 describes a more detailed, exemplary embodiment of steps 102-106 shown in FIG. 1. In steps 202 and 204 the target population and the endpoint of the prognostic reasoning tool are defined and forwarded as input to step 206, in which inclusion and exclusion criteria for the publications are defined. Steps 208 to 216, entail defining the sources of evidence, and search terms defining the target population, endpoints of interest, and characterizing features. At the end of each cycle the literature is qualitatively assessed in order to identify potential new exposure/risk factors.

Once the search strategy and all required definitions are made the publications are screened and graded in steps 218 and 220, respectively, and a final selection of publications for analysis and extraction is made in step 222. The extraction of characterizing features etc. is then performed in step 224.

Figure 3:
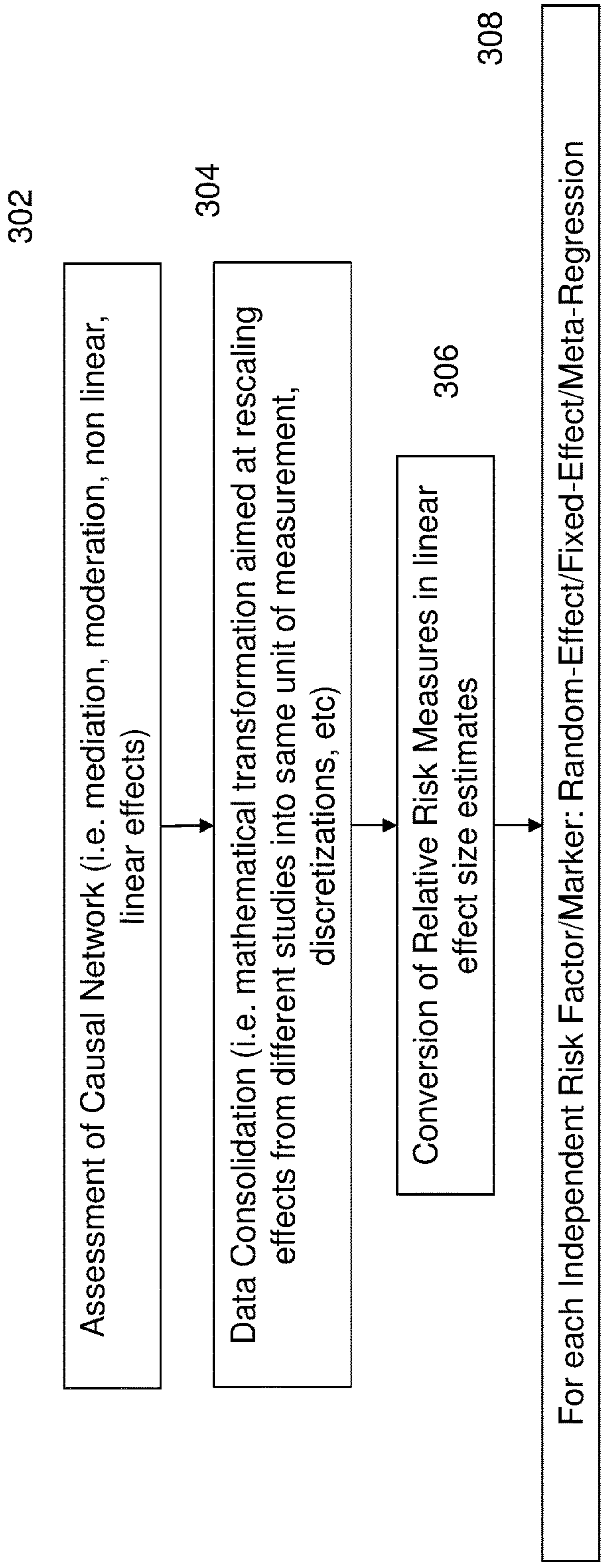
FIG. 3 illustrates a more detailed, exemplary embodiment of the merging and computation steps shown in FIG. 1.

FIG. 3 illustrates a more detailed, exemplary embodiment of merging and computation steps 108 and 110, respectively, shown in FIG. 1. In step 302 an assessment is performed to generate a theory representing the process of causation linking the exposure and the outcome of interest. In steps 304 and 306 the measures of association extracted from the literature are consolidated into a common effect size measure. This may include scaling for different sample sizes, different discretization and the like. At this point, different meta-analytic techniques can be performed for each independent risk factor or marker in step 308.

Figure 4:
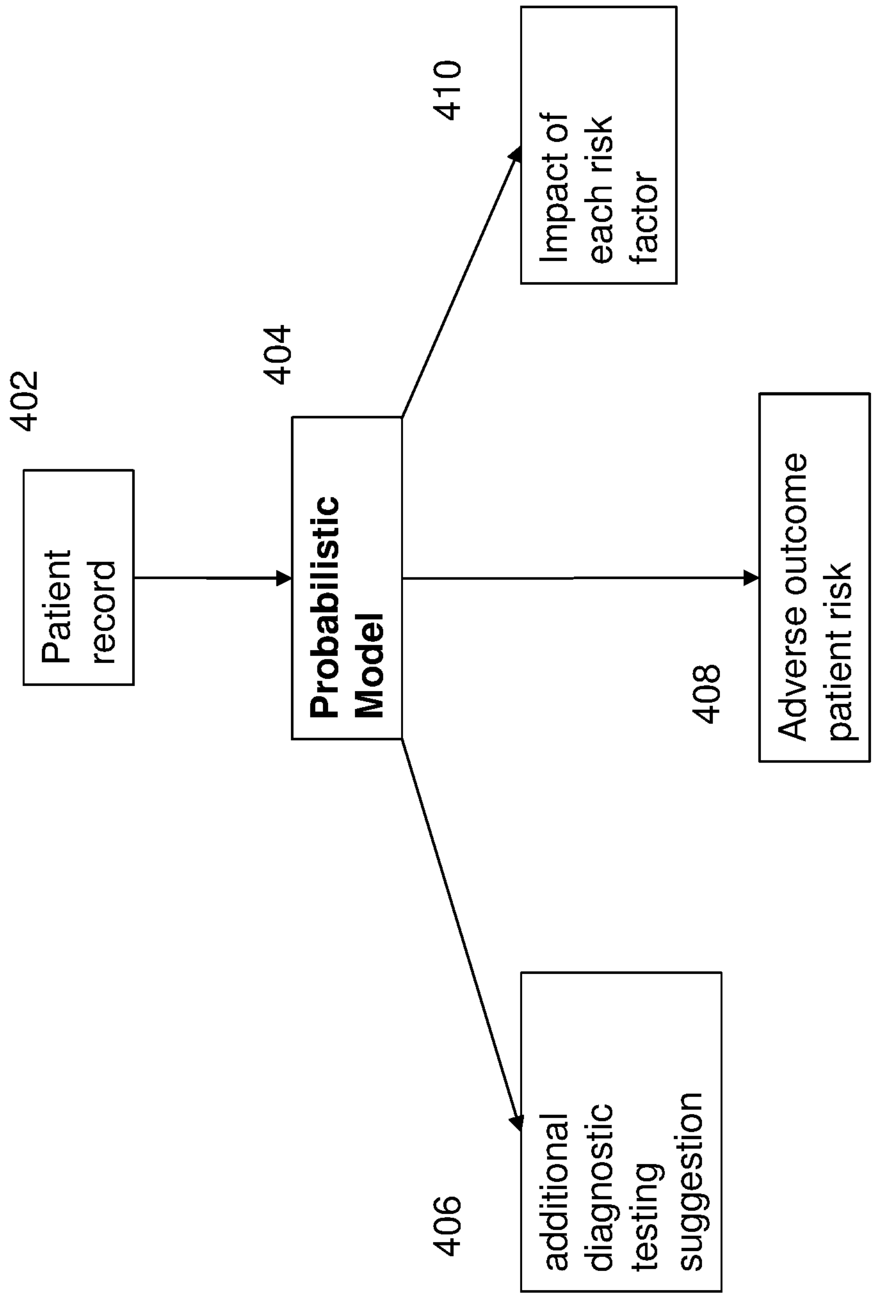
FIG. 4 depicts a data and results flow diagram of an exemplary method of predicting occurrence or progression of a first adverse health condition for an arbitrarily selectable first subpopulation of a total population.

FIG. 4 depicts a data and results flow diagram of an exemplary method of predicting occurrence or progression of a first adverse health condition for an arbitrarily selectable first subpopulation of a total population. In the example the subpopulation is a single patient. Data 402 from a patient record is provided to the generalized probabilistic model 404. Running the analysis using the generalized probabilistic model 404 provides one or more of a suggestion 406 for additional diagnostic testing, an indication representing a patient risk for an adverse health condition 408 and an indication 410 how big the impact of each characterizing feature, or risk factor, is on the patient risk for acquiring or progress of an adverse health condition.

Figure 5:
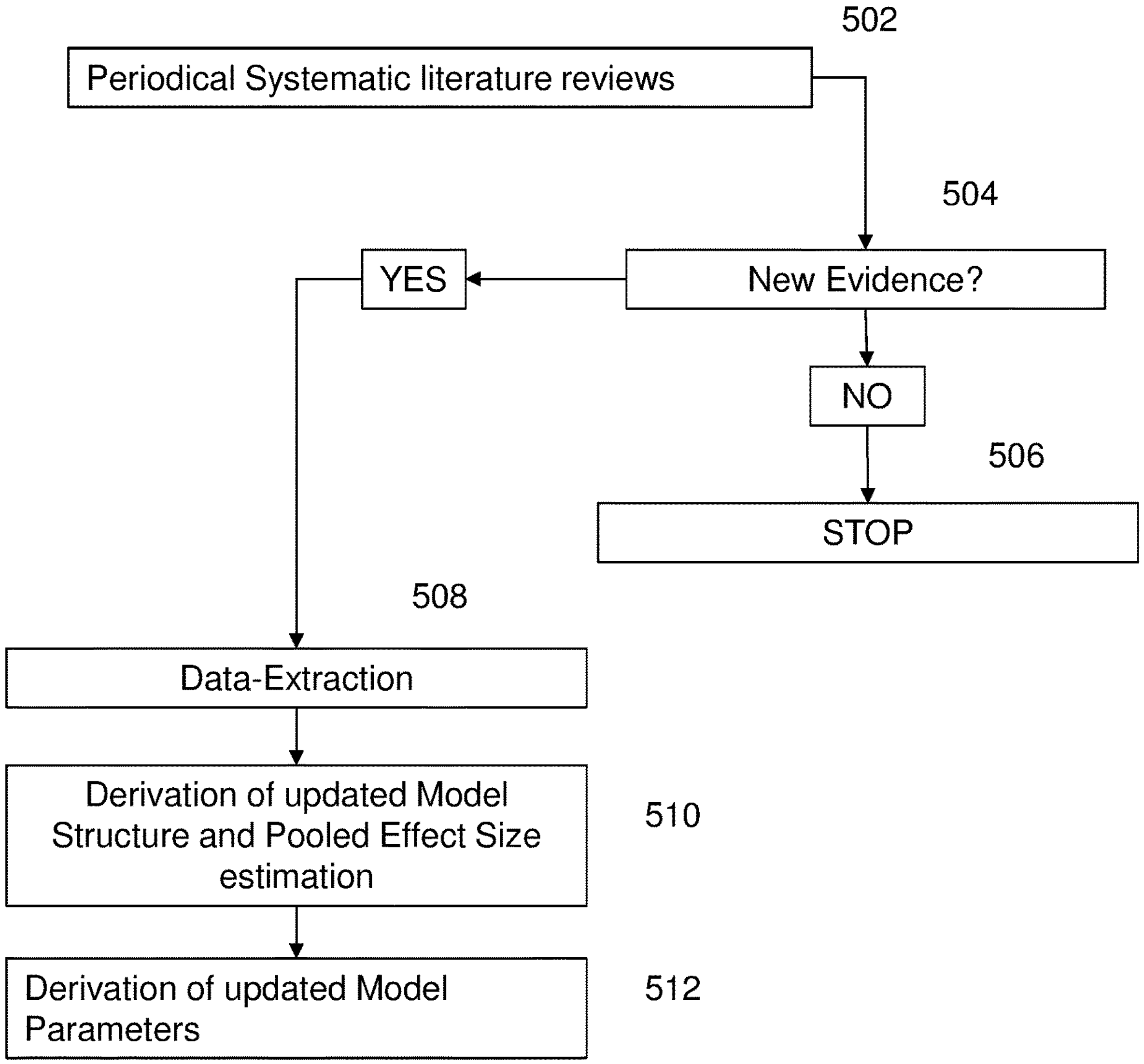
FIG. 5 shows a flowchart diagram of one exemplary aspect of the method of generating a generalized model for adaptively predicting occurrence or progression of a first adverse health condition for a first subpopulation arbitrarily selected from a total population, in which the generalized model is updated by analyzing new publications.

FIG. 5 shows a flowchart diagram of one exemplary aspect of the method of generating a generalized model for adaptively predicting occurrence or progression of a first adverse health condition for a first subpopulation arbitrarily selected from a total population, in which the generalized model is updated by analyzing new publications. Periodical or event-triggered check for new publications is executed in step 502. The review may be performed in the same way as in step 102 of FIG. 1, and appropriate keywords may be determined in the same way as explained with reference to FIG. 2. Whenever a publication is found in step 504 that promises to provide new evidence or generally new data in respect of an adverse health condition, e.g. new subpopulations, new characteristic features, etc., the method follows the "yes"-path to step 508, in which the data extraction is executed, e.g. in the way discussed with reference to FIG. 1. The following steps 510 and 512 likewise may correspond to one or more of steps 106 to 110 discussed with reference to FIG. 1. Updating the generalized model using new publications allows for the model to become more accurate or effective in predicting without having to derive again the full model generation process that was initially required and thus saves time and effort.

Figure 6:
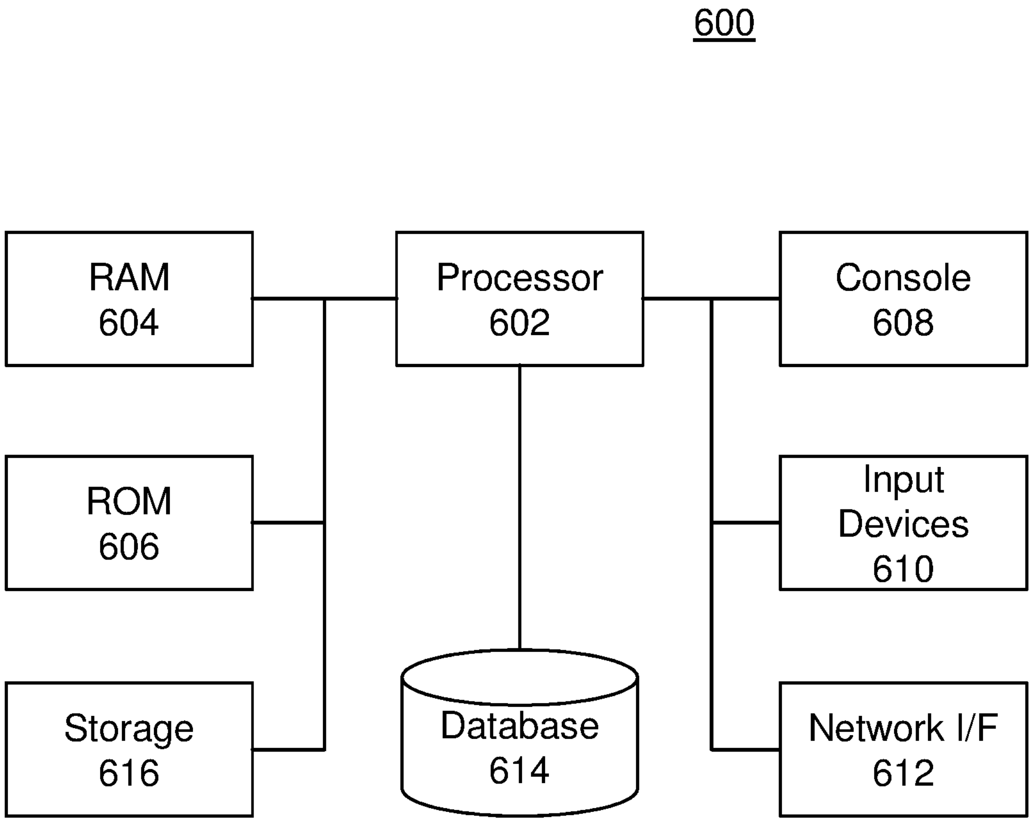
FIG. 6 shows an exemplary computer system adapted to perform one or more aspects of the present method.

FIG. 6 shows an exemplary computer system 600 adapted to perform one or more aspects of the present method. Computer system 600 may include a processor 602, a random access memory (RAM) 604, a read-only memory (ROM) 606, a console 608, input devices 610, network interfaces 612, database 614, and a storage 616. It is understood that the type and number of listed devices are exemplary only and not intended to be limiting. The number of listed devices may be changed and other devices may be added.

Processor 602 may include any appropriate type of general purpose microprocessor, digital signal processor, or microcontroller. Processor 602 may execute sequences of computer program instructions to perform various processes or method steps as explained above. The computer program instructions may be loaded into RAM 604 for execution by processor 602 from a read-only memory (ROM), or from storage 616. Storage 616 may include any appropriate type of mass storage provided to store any type of information that processor 602 may need to perform the processes. For example, storage 616 may include one or more hard disk devices, optical disk devices, or other storage devices to provide storage space.

Console 608 may provide a graphic user interface (GUI) to display information to users of computer system 600. Console 608 may include any appropriate type of computer display device or computer monitor. Input devices 610 may be provided for users to input information into computer system 600. Input devices 610 may include a keyboard, a mouse, or other optical or wireless computer input devices, etc. Further, network interfaces 612 may provide communication connections such that computer system 600 may be accessed remotely through computer networks via various communication protocols, such as transmission control protocol/internet protocol (TCP/IP), hyper text transfer protocol (HTTP), etc.

Database 614 may contain model data and/or any information related to data records under analysis, such as model parameters and testing data. Databases 614 may include any type of commercial or customized databases. Databases 614 may also include analysis tools for analyzing the information in the database. Processor 602 may also use databases 614 to determine and store performance characteristics of the generalized model.

Other embodiments, features, aspects, and principles of the disclosed exemplary medical devices and methods will be apparent to those skilled in the art and may be implemented in various environments and systems.

The invention claimed is:

1. A treatment method comprising controlling an extraction module to adjust, rank, and/or select characterizing features and associated factors in accordance with a value representing a quality of each of a plurality of publications and/or primary clinical data sources stored on one or more electronic databases, subsequently, generating a summary score indicating a risk of occurrence or progression of an adverse health condition for an arbitrarily selectable first subpopulation of a total population comprising a plurality of second subpopulations, the generating comprising running a computer-implemented method that uses a generalized model of adaptively predicting the occurrence or progression of the adverse health condition for the first subpopulation, the computer-implemented method implemented by the execution of computer program instructions of a computer comprising one or more microprocessors, a volatile and/or non-volatile memory, and one or more data and/or user interfaces, the computer being communicatively connected to the one or more electronic databases, the computer-implemented method comprising:

generating the generalized model by controlling the extraction module to identify and extract information about characterizing features of the plurality of second subpopulations, about occurrences and/or severity of the adverse health condition found therein, and/or about corresponding prognostic results, from the plurality of publications and/or primary clinical data sources stored on the one or more electronic databases, wherein the extraction module is configured to identify other characterizing features besides the characterizing features, the other characterizing features being unknown from any one of the plurality of publications and/or primary clinical data sources taken alone, controlling an associator module to associate, from each of the plurality of publications and/or primary clinical data sources, one or more of the characterizing features identified therein with corresponding first factors indicating a relation with an adverse or beneficial contribution of the characterizing feature to the occurrence or progression of the adverse health condition, and further to associate one or more of the characterizing features with corresponding second factors indicating the relative frequency of occurrence in the respective second subpopulation considered in the respective publication, controlling a combiner module to combine the characterizing features and their first and second factors into a generalized model for the total population, wherein the combining includes calculating a baseline risk for a general member of the total population, and controlling a communication module to store the generalized model including the calculated baseline risk for a general member of the total population, in a retrievable manner on a computer accessible and readable medium;

controlling the communication module to receive one or more characterizing features from the generalized model generated and stored in the computer accessible and readable memory;

controlling the communication module to receive data characterizing the first subpopulation; and controlling the communication module to provide the one or more received characterizing features from the generalized model and the data characterizing the first subpopulation to a predictor module implementing a probabilistic model, which probabilistic model produces, as an output signal, a summary score indicating a risk of occurrence or progression of the adverse health condition for the first subpopulation, wherein the first subpopulation includes a patient, and the treatment method further comprises determining that the patient has a probability of acquiring the adverse health condition, by using the summary score, and treating the patient by providing an effective treatment or preventive measure that is focused on the adverse health condition with which the patient is determined to have a probability of acquiring.

2. The treatment method of claim 1, further including controlling the extraction module to implement one or more of electronic text processing, optical character recognition, and natural language processing.

3. The treatment method of claim 1, further including adjusting, ranking and/or selecting the characterizing features and the associated factors in accordance with a value representing a conditional probability of an outcome associated with a single characterizing feature across the plurality of publications and/or primary clinical data sources.

4. The treatment method of claim 1, further including adjusting, ranking and/or selecting the characterizing features and the associated factors in accordance with a received prediction time target or for at least one preset prediction time target.

5. The treatment method of claim 1, further including adjusting, ranking and/or selecting the characterizing features and the associated factors in accordance with a received current stage or severity of the adverse health condition in the first subpopulation or for at least one preset stage or severity.

6. The treatment method of claim 1, further including, in a first run of the method, limiting the plurality of publications and/or primary clinical data sources to those considering the adverse health condition and, in a second run of the method, using the result of the first run as an input to the method, along with one or more publications and/or primary clinical data sources not considering the adverse health condition.

7. The treatment method of claim 1, wherein the predictor module is further configured to adjust, rank and/or select the characterizing features and the associated factors in accordance with a current stage or severity of the adverse health condition in the first subpopulation received as a further input.

8. The treatment method of claim 1, further including providing the one or more characterizing features and their positive or negative effect on the risk or the probability of occurrence or progression of the adverse health condition in a ranked order according to their significance of their contribution to the summary score.

9. The treatment method of claim 8, further including:
- highlighting those characterizing features having positive or negative effect on the risk or the probability of occurrence or progression of the adverse health condition, which can be modified or influenced through one or more responsive actions, to provide a recommendation; and
- adapting the treating of the patient to include a patient-specific adaptation, based on the recommendation, wherein the patient-specific adaptation is selected from a specific therapy, a specific change of lifestyle, a specific change of diet, and a specific medical intervention.

10. The treatment method of claim 9, further including providing information about how much the risk or the probability of occurrence or progression of the adverse health condition is modified by the one or more responsive actions.

11. The treatment method of claim 1, further including providing a selection of therapy recommendations based on the kind of health condition that the adverse health condition is, and/or the risk score.

12. The treatment method of claim 1, further including providing a selection of additional diagnostic tests and/or therapy that could produce data related to or describing further characterizing features, which can be provided to the predictor module for improving the accuracy of the summary score.

13. The treatment method of claim 12, further including providing the selection of additional diagnostic tests and/or therapy in a ranked order.

14. The treatment method according to claim 1, wherein the patient has an abdomen and a blood system, the adverse health condition is chronic kidney disease, and the method further comprises:
- predicting progression of the chronic kidney disease, based on the summary score, to form a prediction;
- determining when to prepare the patient for a renal supplement or replacement therapy, based on the prediction;
- subsequently preparing the patient for a renal supplement or replacement therapy, wherein the renal supplement or replacement therapy is to be performed at a time that is based on the prediction; and
- performing surgery to place a catheter in the abdomen or to create a fistula, graft, or other access point, to the blood system, at the time that is based on the prediction.

15. The treatment method according to claim 1, wherein the patient has an abdomen and a blood system, the adverse health condition is end stage renal disease, and the method further comprises:
- predicting progression of the end stage renal disease, based on the summary score, to form a prediction;
- determining when to prepare the patient for a renal supplement or replacement therapy, based on the prediction;
- subsequently preparing the patient for a renal supplement or replacement therapy, wherein the renal supplement or replacement therapy is to be performed at a time that is based on the prediction; and
- performing surgery to place a catheter in the abdomen or to create a fistula, graft, or other access point, to the blood system, at the time that is based on the prediction.

16. The treatment method according to claim 1, wherein the patient has an abdomen and a blood system, the adverse health condition is kidney failure, and the method further comprises:
- predicting progression of the kidney failure, based on the summary score, to form a prediction;
- determining when to prepare the patient for a renal supplement or replacement therapy, based on the prediction;
- subsequently preparing the patient for a renal supplement or replacement therapy, wherein the renal supplement or replacement therapy is to be performed at a time that is based on the prediction; and
- performing surgery to place a catheter in the abdomen or to create a fistula, graft, or other access point, to the blood system, at the time that is based on the prediction.

17. The treatment method according to claim 1, wherein the adverse health condition is a cardiovascular event, and the method further comprises:
- predicting an occurrence of the cardiovascular event, based on the summary score, to form a prediction;
- determining when to prepare the patient for a treatment to mitigate or eliminate a risk of hospitalization due to the cardiovascular event, based on the prediction; and
- treating the patient, at a time that is based on the prediction, to mitigate or eliminate the risk of hospitalization due to the cardiovascular event, wherein the treating comprises administering a therapy comprising a change of lifestyle, a change of diet, and/or medical intervention.

18. The treatment method according to claim 1, further comprising, subsequent to the step of controlling the communication module to provide the one or more received characterizing features from the generalized model and the data characterizing the first subpopulation to the predictor module implementing the probabilistic model:
- further controlling the associator module to associate at least one of the other characterizing features from the plurality of publications and/or primary clinical data sources, with corresponding first factors indicating a relation with an adverse or beneficial contribution of the at least one other characterizing feature to the occurrence or progression of the adverse health condition, and to associate the at least one other characterizing feature with corresponding second factors indicating the relative frequency of occurrence in the respective second subpopulation considered in the respective publication; and
- further controlling the combiner module to combine the at least one other characterizing feature and its corresponding first and second factors, into the generalized model.

19. A medical device configured to adaptively predict occurrence or progression of an adverse health condition for an arbitrarily selectable first subpopulation of a total population that comprises a plurality of second subpopulations, the medical device comprising a display, a microprocessor, a volatile and/or non-volatile memory, and one or more data and/or user interfaces, the medical device comprising or cooperating with one or more electronic databases, and the medical device further comprising:

a model generator that is configured to (1) adjust, rank, and/or select characterizing features and associated factors in accordance with a value representing a quality of each of a plurality of publications and/or primary clinical data sources in the one or more electronic databases, and (2) generate a generalized model for adaptively predicting occurrence or progression of a specific adverse health condition for the arbitrarily selected first subpopulation of the total population that comprises a plurality of second subpopulations, the model generator and/or its constituent components comprising, or cooperating with, the microprocessor, the volatile and/or non-volatile memory, and the one or more data and/or user interfaces, and further comprising an extraction module adapted to identify and extract information about characterizing features of the plurality of second subpopulations, about occurrences and/or severity of the adverse health condition found therein, and/or about corresponding prognostic results, from the plurality of publications and/or primary clinical data sources stored in the one or more electronic databases, wherein the extraction module is configured to identify other characterizing features besides the characterizing features, the other characterizing features being unknown from any one of the plurality of publications and/or primary clinical data sources taken alone, an associator module adapted to associate, from each of the plurality of publications and/or primary clinical data sources, one or more of the characterizing features identified therein with corresponding first factors indicating a relation with an adverse or beneficial contribution of the characterizing feature to the occurrence or progression of the adverse health condition, and further associating one or more of the characterizing features with corresponding second factors indicating the relative frequency of occurrence in the respective second subpopulation considered in the respective publication, and a combiner module adapted to combine the characterizing features and their first and second factors into a generalized model for the total population, wherein the combining includes calculating a baseline risk for a general member of the total population;

a communication module adapted to store the generalized model, including the calculated baseline risk for a general member of the total population, in a retrievable manner on a computer accessible and readable medium, configured to receive an input identifying or selecting the adverse health condition and the generalized model that is generated and stored in the computer accessible and readable medium and that is adapted to the adverse health condition as well as one or more characterizing features used in the generalized model, and further configured to receive corresponding data characterizing the first subpopulation; and a predictor module configured to process the one or more characterizing features received in accordance with the generalized model and the data characterizing the first subpopulation, wherein the predictor module includes computer program instructions executable by a computer implementing a probabilistic model, wherein the probabilistic model and/or parameters thereof are selected or adapted in accordance with the adverse health condition, wherein the predictor module is configured to apply the probabilistic model in accordance with the received generalized model, apply the characterizing features and data characterizing the first subpopulation, and output a summary score predicting a risk or probability of occurrence or progression of the adverse health condition in the first subpopulation, wherein the communication module is further configured to provide, to a user or a further computer system, the summary score and/or one or more characterizing features and their positive or negative effect on the predicted risk or probability of occurrence or progression of the adverse health condition, and the medical device is configured to provide a selection of additional diagnostic tests and/or therapy based on the summary score.

20. The medical device of claim 19, wherein the model generator further comprises a priming module adapted to receive input corresponding to selecting a specific adverse health condition and/or a severity or current stage of the adverse health condition, wherein the specific adverse health condition selected and/or the severity or current stage of the adverse health condition is used for selecting one of a variety of statistical models for generating the generalized model.

21. The medical device of claim 19, with the model generator further configured to adjust, rank and/or select the characterizing features and the associated factors in accordance with a value representing a conditional probability of an outcome associated with a single characterizing feature across the plurality of publications and/or primary clinical data sources.

22. The medical device of claim 19, with the model generator further configured to adjust, rank and/or select the characterizing features and the associated factors in accordance with a received prediction time target or for at least one preset prediction time target.

23. The medical device of claim 19, with the model generator further configured to adjust, rank and/or select the characterizing features and the associated factors in accordance with a received current stage or severity of the adverse health condition in the first subpopulation or for at least one preset stage or severity.

24. The medical device of claim 19, with the model generator further configured to, in a first run, control the extraction module to limit the plurality of publications and/or primary clinical data sources to those actually considering the adverse health condition and, in a second run, use the result of the first run as an input, along with one or more publications and/or primary clinical data sources not considering the adverse health condition.

25. The medical device of claim 19, wherein the predictor module is further configured to adjust, weight, rank and/or select the characterizing features and the associated factors in accordance with a current stage or severity of the adverse health condition in the first subpopulation received as a further input.

26. The medical device of claim 19, wherein the predictor module or the communication module is further configured to provide the one or more characterizing features and their positive or negative effect on the risk or the probability of occurrence or progression of the adverse health condition in a ranked order according to their significance of their contribution to the summary score.

27. The medical device of claim 19, wherein the communication module is further configured to highlight those characterizing features having positive or negative effect on the risk or the probability of occurrence or progression of the adverse health condition, which can be modified or influenced through one or more responsive actions from the non-exhaustive list comprising therapy, change of lifestyle, change of diet and medical intervention.

28. The medical device of claim 19, wherein the predictor module or the communication module is further configured to provide information about how much the risk or the probability of occurrence or progression of the adverse health condition is modified by a responsive action.

29. The medical device of claim 19, wherein the communication module is further configured to provide a selection of therapy recommendations based on the kind of adverse health condition and/or the risk score in response to a request issued to a database, or artificial intelligence system connected thereto, the database storing at least one therapy recommendation for each one of a plurality of adverse health conditions.

30. The medical device of claim 19, wherein the predictor module is further configured to provide, through the communication module, a selection of additional diagnostic tests and/or therapy that could produce data related to or describing further characterizing features, which can be provided to the predictor module for improving the accuracy of the summary score.

* * * * *